United States Patent [19]
Kuma et al.

[11] Patent Number: 5,869,306
[45] Date of Patent: Feb. 9, 1999

[54] GENE TRANSFER PREPARATION

[75] Inventors: Hidekazu Kuma; Osamu Iijima; Yosuke Suzuki, all of Ibaraki-ken, Japan

[73] Assignee: Hisamitsu Pharmaceutical Co., Inc., Saga, Japan

[21] Appl. No.: 913,592
[22] PCT Filed: Mar. 15, 1996
[86] PCT No.: PCT/JP96/00652
§ 371 Date: Sep. 12, 1997
§ 102(e) Date: Sep. 12, 1997
[87] PCT Pub. No.: WO96/29096
PCT Pub. Date: Sep. 26, 1996

[30] Foreign Application Priority Data

Mar. 17, 1995 [JP] Japan ......................... 7-59261

[51] Int. Cl.$^6$ .................................. C12N 15/64
[52] U.S. Cl. ......................... 435/172.3; 435/320.1
[58] Field of Search .................. 435/172.3, 320.1

[56] References Cited

U.S. PATENT DOCUMENTS 5,292,653  3/1994  Kit et al. ......................... 435/235.1
5,681,746  10/1997  Bedner et al. ..................... 435/350

FOREIGN PATENT DOCUMENTS

WO 90/11359  10/1990  WIPO .
WO 94/21806  9/1994  WIPO .

OTHER PUBLICATIONS

European Search Report dated 15 May 1998.

Venkatesh et al., "Selective induction of toxicity to human cells expressing human immunodeficiency virus type 1 Tat by a conditionally cytotoxic adenovirus vector," *Proc. Natl. Acad. Sci. USA* 87:8746–8750 (1990).

Poznansky et al., "Gene Transfer into Human Lymphocytes by a Defective Human Immunodeficiency Virus Type 1 Vector," *Journal of Virology* 65:532–536 (1991).

Brady et al., "Specific ablation of human immunodeficiency virus Tat-expressing cells by conditionally toxic retroviruses," *Proc. Natl. Acad. Sci. USA* 91:365–369 (1994).

Biasolo et al., "Gene therapy of AIDS: inhibition of HIV by retroviral vectors," *ECB6: Proceedings of the 6th European Congress on Biotechnology*: 685–688, 1994, Elsevier Science B.V.

Caruso et al., "HIV-triggered killing of booby trapped cells prevents viral spread in an HIV-infected cell population," *Bone Marrow Transplantation* 9(Suppl. 1):187–188, 1992.

"Improved Methods of Retroviral Vector Transduction and Production for Gene Therapy", Kotani et al. *Human Gene Therapy*, vol. 5, 1994, pp. 19–28.

English language translation and copy of "Experimental Techniques in Virology", revised second edition, General Principles, Edited by the Research Fellow Association, National Institute of Health, Japan, and published by Maruzen Co., Ltd.

*Primary Examiner*—James Ketter
*Attorney, Agent, or Firm*—Morrison & Foerster, LLP

[57] ABSTRACT

A process for producing a gene transfer preparation which comprises adding one or more additives selected from among arginine, glutamic acid or its sodium salt, serine, glucose, inositol, lactose, mannitol, sorbitol, trehalose and xylose to a recombinant virus vector followed by freeze-drying.

3 Claims, 3 Drawing Sheets

GENE TRANSFER PREPARATION

TECHNICAL FIELD

This invention relates to a process for producing a freeze-dried preparation of a virus vector for gene therapy which is excellent in safety and storage stability and a gene transfer preparation obtained by this process.

BACKGROUND ART

Owing to the rapid progress in genetic engineering, there have been developed various molecular biological processes. With these developments, techniques for analyzing genetic information and gene functions have been remarkably advanced. As a result, a number of attempts have been made to feed back the results thus achieved into actual clinical treatments. One of the most remarkable advances has been achieved in the field of gene therapy. That is to say, there have been successfully identified and decoded genes causative of various hereditary diseases. On the other hand, techniques have been established for physically or chemically transferring these genes into cells. Accordingly, gene therapy has already completed the stage of fundamental experiments and thus reached the stage of clinical application.

Since the first clinical test on gene therapy was performed in 1989 in the United States, gene therapy has been already applied to clinical tests in Italy, the Netherlands, France, England and China. In the United States, in particular, the Recombinant DNA Committee (RAC) of NIH has approved 54 gene therapy protocols by July 1994 and, therefore, attempts have been made to apply gene therapy to the treatment of hereditary diseases such as congenital immunological deficiency (adenosine deaminase deficiency), familial hypercholesterolemia and cystic fibrosis and various types of cancer such as malignant melanoma and glioma. Moreover, a number of fundamental studies on the gene therapy for AIDS have been made in recent years.

Gene therapy is classified into germline cell gene therapy and somatic cell gene therapy depending on the type of the target cells to which genes are to be transferred. From another point of view, it is classified into augmentation gene therapy wherein a new (normal) gene is added while leaving the abnormal (causative) gene as such and replacement gene therapy wherein the abnormal gene is replaced by the normal one. At the present stage, the augmentation gene therapy on somatic cells is exclusively effected due to ethical and technical restrictions. A gene therapy process performed today comprises taking out the target cells from the body and, after the completion of the gene transfer, putting the cells back into the body again through self-transplantation (i.e., ex vivo gene therapy). Further, it is now under consideration to administer genes directly to patients in future (i.e., in vivo gene therapy).

One of the large problems in the clinical application of gene therapy is how to safely and efficiently introduce a foreign gene into the target cells. Although it was tried to employ physical procedures such as microinjection early in the 1980's, only a poor transfer efficiency could be established and genes could not be transferred in a stable state thereby. Furthermore, the limited techniques for cell incubation on a mass scale in those days made it impossible to put such attempts into practical use. Subsequently, there were developed recombinant viruses (virus vectors) for efficiently transferring foreign genes into target cells, which made it possible for the first time to apply the gene therapy to clinical purposes.

There are several types of virus vectors as will be described hereinbelow. The virus vectors most frequently employed in the gene therapy today are retrovirus vectors originating in moloney murine leukemia virus (MoMLV). That is to say, genes are transferred by taking advantage in the propagation manner of this virus. A retrovirus is an RNA virus having an envelope which invades into cells through the bond of the envelope protein to the receptor in the host cell side. After the invasion, the single-stranded virus RNA is converted into a double-stranded DNA via a reverse transcriptase and thus integrated into the genomic DNA of the infected cells in a stable state, though at random. However, the integration cannot be completed unless the cells are dividing and proliferating [Miller D. G., et al., Molecular and Cellular Biology, 10 (8), 4239 (1990)]. The retrovirus gene thus integrated is called a provirus. From this provirus, RNA is transcribed and thus viral proteins are synthesized. Then new viral particles are formed from these proteins and the virus RNA. In a retrovirus vector, the retrovirus gene in the above-mentioned case recombines with a foreign gene [Miller A. D., Current Topics in Microbiology and Immunology, 158, 1 (1992)]. On the MoMLV vector, a number of studies have been carried out hitherto and many improvements have been achieved on the safety thereof. As a result, no serious trouble has occurred so far. With respect to the MoMLV vector, however, it is known that the gene is integrated into the genomic DNA of the target cells at random and the long terminal repeat (hereinafter referred to simply as LTR) sustains the promotion activity for expressing the gene. Therefore, it cannot be denied that the random integration of the foreign gene might happen to activate an oncogen existing therearound by chance so as to cause carcinogenesis in the target cells, though there has never been reported such a case so far. Thus, it has been urgently required to develop vectors with improved safety. From a practical viewpoint, the most serious problem regarding the MoMLV vector resides in that a gene cannot be transferred thereby into cells which are not under division. This fact makes gene repair in neuroblasts impossible in a number of congenital metabolic errors. Moreover, hematopoietic stem cells, liver cells, muscle cells, etc. to be treated by gene therapy are usually on the stationary stage in most cases and thus a gene can be transferred thereinto only at a low efficiency. Although cells taken off from the body are subjected to treatments for promoting division so as to elevate the gene transfer efficiency, it is seemingly difficult to transfer a gene into the above-mentioned cells in vivo. Therefore, it is required to develop vectors ensuring efficient gene transfer into cells not being under division too in future.

Although herpes virus vectors are expected as being usable in the transfer of a foreign gene into neuroblasts [Palella, T. D., et al., Mol. Cell. Biol., 8, 457, (1988)], the potent cytotoxicity and large genomic size (150 kb) disturb the development thereof.

HIV vectors have been developed as vectors which enable specific gene transfer into CD4-positive T lymphocytes owing to the host characteristics of the virus per se [Shimada, T., et al., J. Clin. Invest., 88, 1043 (1991)]. Since lymphocytes serve as important target cells in gene therapy for congenital immunological deficiency, AIDS, cancer, etc., expections are placed on the usefulness of the HIV vectors. The largest disadvantage of the HIV vectors resides in that they might be contaminated with wild strains. If this problem could be solved, the HIV vectors might be employed in gene therapy in vivo via intravascular administration.

Further, adenovirus vectors have attracted public attention, since they enable gene transfer into cells which are not under division and can be easily concentrated to a level of about $10^{10}$. Recent studies indicate that genes can be transferred in vivo at a high ratio into airway epithelial cells, liver cells, muscular cells, etc. by using these adenovirus vectors [Lavrero, L. D., et. al., Hum. Gene Therapy, 1, 241 (1990); Quantin, B., Proc. Natl. Acad. Sci. U.S.A., 89, 2581 (1992)]. On the other hand, such an adenovirus vector essentially has a characteristic that a foreign gene is not integrated into the genomic DNA of the target cells. After treating the target cells with the vector, therefore, the effects of the gene transfer can be sustained only for several weeks or several months at the longest. Accordingly, it is required to repeat the gene transfer, which brings about some problems such as increased physical and mental stress for the patient, a decrease in the gene transfer efficiency due to the appearance of anti-adenovirus antibody, etc. In addition, clinical attempts have been already initiated to administer an adenovirus vector with a bronchoscope for treating cystic fibrosis. However, it is reported that inflammatory responses arise in these cases due to the immunogenicity and cytotoxicity of the adenoviral particles.

In contrast, adeno-associated virus (AAV) vectors are characterized in that a foreign gene is integrated into the genomic DNA of the target cells and the vectors have neither any pathogenicity nor cytotoxicity [Muzyczka, N., Currnet Topics in Microbiology and Immunology, 158, 97 (1992)]. Moreover, the ITR (inverted terminal repeat) thereof, which is needed in packaging viral particles and gene integration into genomic DNA, has no promoting activity for gene expression. Thus, the gene expression can be arbitrarily switched on/off by setting an appropriate inner promoter or a tissue-specific promoter can be employed. In the case of the AAV vectors, use can be made of hosts over a wide range, which makes these vectors applicable to various target cells/diseases. Owing to these characteristics, the AAV vectors are expected as novel virus vectors, i.e., a substitute for the MoMLV vectors. It is also found that AAV of wild type is integrated into a definite site in the 19th chromosome [Suwadogo, M. and Roeder, R. G., Prc. Natl. Acad. Sci. U.S.A, 82, 4394 (1985)]. Thus AAV vectors attract public attention as vectors capable of targeting the gene integration site.

However, any manufacturing pharmaceutical discussion has been made on none of these virus vectors in order to storage them in a stable state and maintain the uniformity thereof. Although virus vectors are stored in a frozen state today, the storage period is limited and it is observed that the virus vectors suffer from a decrease in titer with the passage of time. In practical clinical studies, it is therefore needed to prepare a vector in each test and examine the decrease in the gene transfer efficiency during the storage prior to the treatment. Since such examinations comprise complicated procedures and take a considerably long time, it has been strongly required to establish a method for supplying stabilized virus vectors having improved and uniform performance.

It was attempted to freeze-dry MoMLV vectors by using gelatin as a stabilizer [Kotani, H., et al., Human Gene Therapy, 5, 19 (1994)]. Since gelatin usually originates in animals such as swine, it might serve as an immunogen at a high possibility when administered in vivo. Thus, the above method cannot be always referred to as a safe one.

In clinical studies on gene therapy performed today, detailed examinations are made on the type of vectors and the pharmacological effects of genes for therapeutic use. Because they are preparations for gene therapy, virus vectors should be supplied safely so as to ensure a uniform performance. Namely, it is essentially required to establish a process for storing these vectors in a stable state. However, few studies have been made in this field.

DISCLOSURE OF THE INVENTION

The present inventors have conducted extensive studies to solve the above-mentioned problems. As a result, they have successfully established a technique for stably supplying virus vectors having high safety and uniform performance, i.e., a technique for storing virus vectors in a stable state, thus making it possible to freeze-dry various virus vectors without lowering the gene transfer efficiency.

It is known that several types of viruses would not lose their infectivity even after freeze-drying. In such a case, it has been a practice to add gelatin and saccharides thereto. On the other hand, attempts have been also made to freeze-dry virus vectors similar to these viruses. In these cases, gelatin and saccharides are added too. However, it cannot always be considered as a safe method, since there arises a fear that these additives might serve as an immunogen at a high possibility when administered in vivo.

Under these circumstances, it has been attempted in the present invention to develop a freeze-drying method whereby a high gene transfer efficiency can be sustained not by using gelatin, etc. which might serve as an immunogen but by using exclusively low-molecular-weight substances which have been already employed as pharmaceutical additives.

Accordingly, the present invention provides a process for producing a gene transfer preparation which comprises adding one or more additives selected from among arginine, glutamic acid or its sodium salt, serine, glucose, inositol, lactose, mannitol, sorbitol, trehalose and xylose to a recombinant virus vector followed by freeze-drying.

The present invention further provides a gene transfer preparation produced by the above-mentioned process.

BEST MODE FOR CARRYING OUT THE INVENTION

Figure 1:
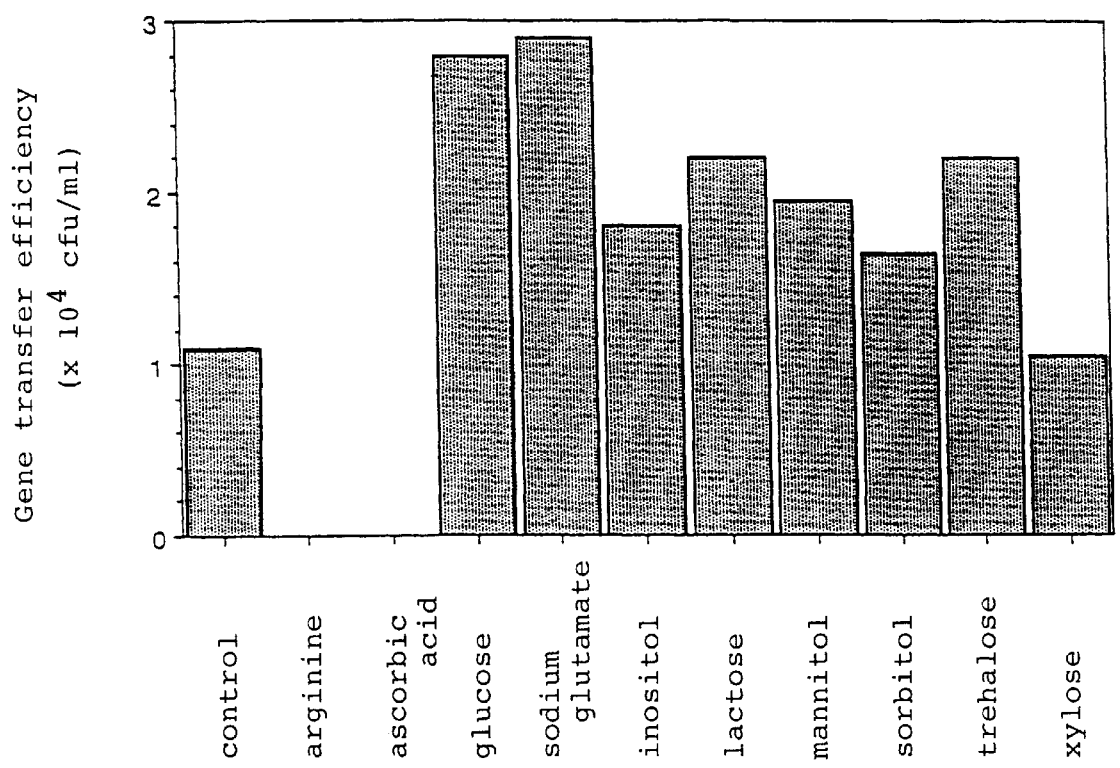
FIG. 1 is a graph which shows gene transfer efficiencies achieved by adding various additives each at a concentration of 5%.

The virus vector to be used in the present invention may be an arbitrary one usable in gene therapy selected from among, for example, the above-mentioned moloney murine leukemia virus (MoMLV) vectors, herpes virus vectors, adenovirus vectors, adeno-associated virus vectors and human immunodeficiency virus (HIV) vectors. Such a vector is dissolved in a medium such as DMEM medium or PBS to thereby give a virus vector stock solution. The virus vector stock solution may have an arbitrary concentration.

The process of the present invention can be achieved by adding additive(s) to the above-mentioned virus vector stock solution and freeze-drying the same. It is preferable that the additives to be used in the present invention are less immunogenic substances such as low-molecular-weight amino acids, derivatives thereof, saccharides and derivatives thereof.

Preferable examples of the amino acids and derivatives thereof include arginine, glutamic acid or its sodium salt and serine. Among all, glutamic acid or its sodium salt is particularly preferable therefor.

Preferable examples of the saccharides and derivatives thereof include glucose, inositol, lactose, mannitol, sorbitol, trehalose and xylose. Among all, glucose is the most desirable example thereof.

One or more substances selected from these amino acids and saccharides may be freely combined and employed as the additive(s) depending on the type of the virus vector employed, the concentration of the virus vector stock solution, etc. Selection can be made of a combination of an amino acid with another amino acid, a saccharide with another saccharide, or an amino acid with a saccharide. Among all, the combination of sodium glutamate with glucose is the most desirable one, since a high gene transfer efficiency (virus vector titer) can be maintained thereby.

Each additive selected from amino acids and saccharides is used at a weight ratio to the vector solution of from about 1% to about 10%, preferably from about 1.5% to about 7% and still preferably from about 1.5% to about 5%.

The solution may further contain ascorbic acid, polyethylene glycol, polyvinylpyrrolidone, polyvinyl alcohol, preservatives, etc. Since it is preferable that the virus vector solution is isotonic, the osmotic pressure of the solution can be controlled by adding a buffer thereto.

The thus obtained virus vector solution containing various additives is freeze-dried. Freeze-drying can be performed by a publicly known method. For example, the virus vector solution is frozen with liquid nitrogen and then treated with a freeze-dryer (manufactured by Finaqua). The freeze-dried gene transfer preparation was then packed in vials and stored preferably at low temperatures till using. The gene transfer preparation of the present invention can be reconstituted with water before using. As will be shown in the Examples hereinafter, the virus vector reconstituted with water sustained a high gene transfer efficiency.

The present invention makes it possible to obtain a gene transfer preparation sustaining a high gene transfer efficiency by using not any ingredient likely to serve as an immunogen (gelatin, etc.) but exclusively low-molecular-weight substances which have been already employed as pharmaceutical additives. The gene transfer preparation of the present invention can be easily stored and sustains a high titer. Therefore, it is usable in every virus vector preparation and has a very broad application range.

EXAMPLES

To further illustrate the present invention in greater detail, and not by way of limitation, the following Examples will be given.

Example 1

Preparation of recombinant MoMLV vector

A cell culture dish (9 cm in diameter) was inoculated with PA317/β-19 (provided by Prof. Shimada, Nippon Medical School) capable of producing a recombinant MoMLV vector containing neomycin resistance gene. Then these cells were incubated in DMEM medium (manufactured by Gibco) containing 10% of fetal calf serum (manufactured by Gibco) under usual conditions (37° C., 5% $CO_2$) up to about 80% confluence. Subsequently, the medium was replaced and, 12 hours thereafter, the medium containing the recombinant MoMLV vector was recovered and referred to as the virus vector stock solution.

Example 2

Preparation and freeze-drying of recombinant MoMLV vector solution

Figure 2:
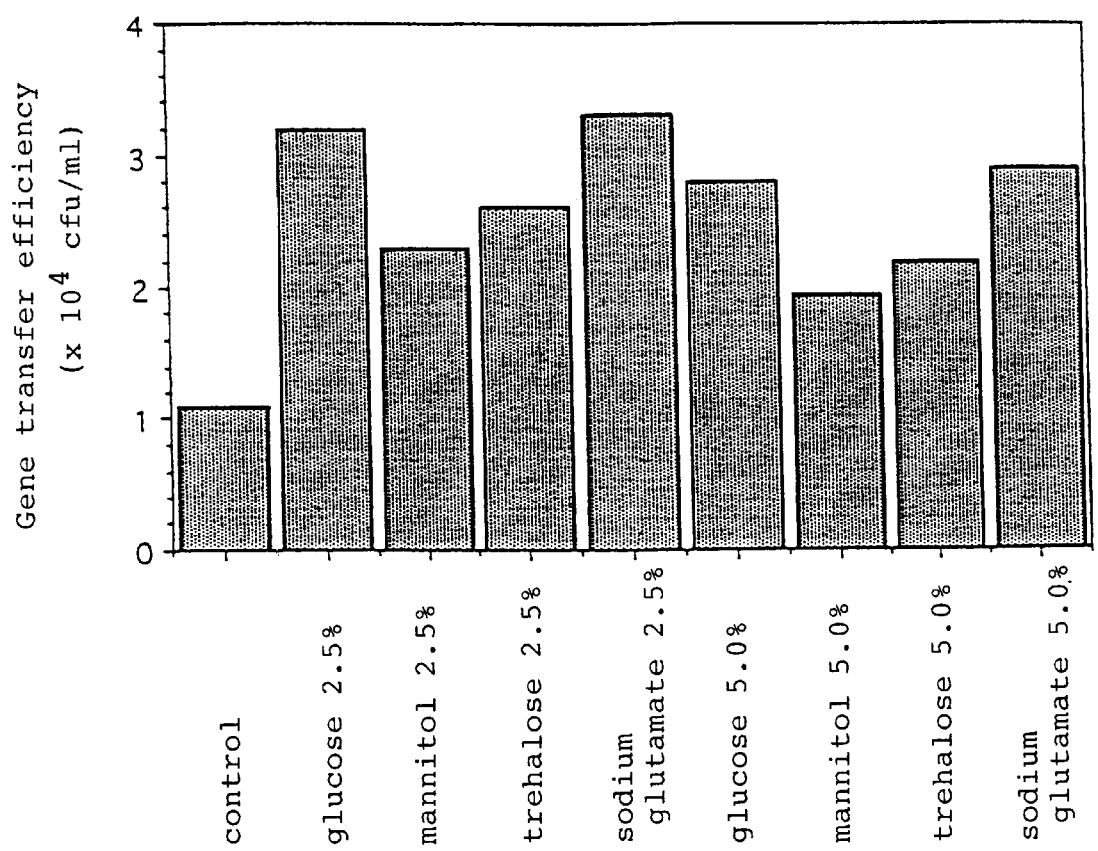
FIG. 2 is a graph which shows gene transfer efficiencies achieved by adding various additives each at concentrations of 2.5% and 5%.
Figure 3:
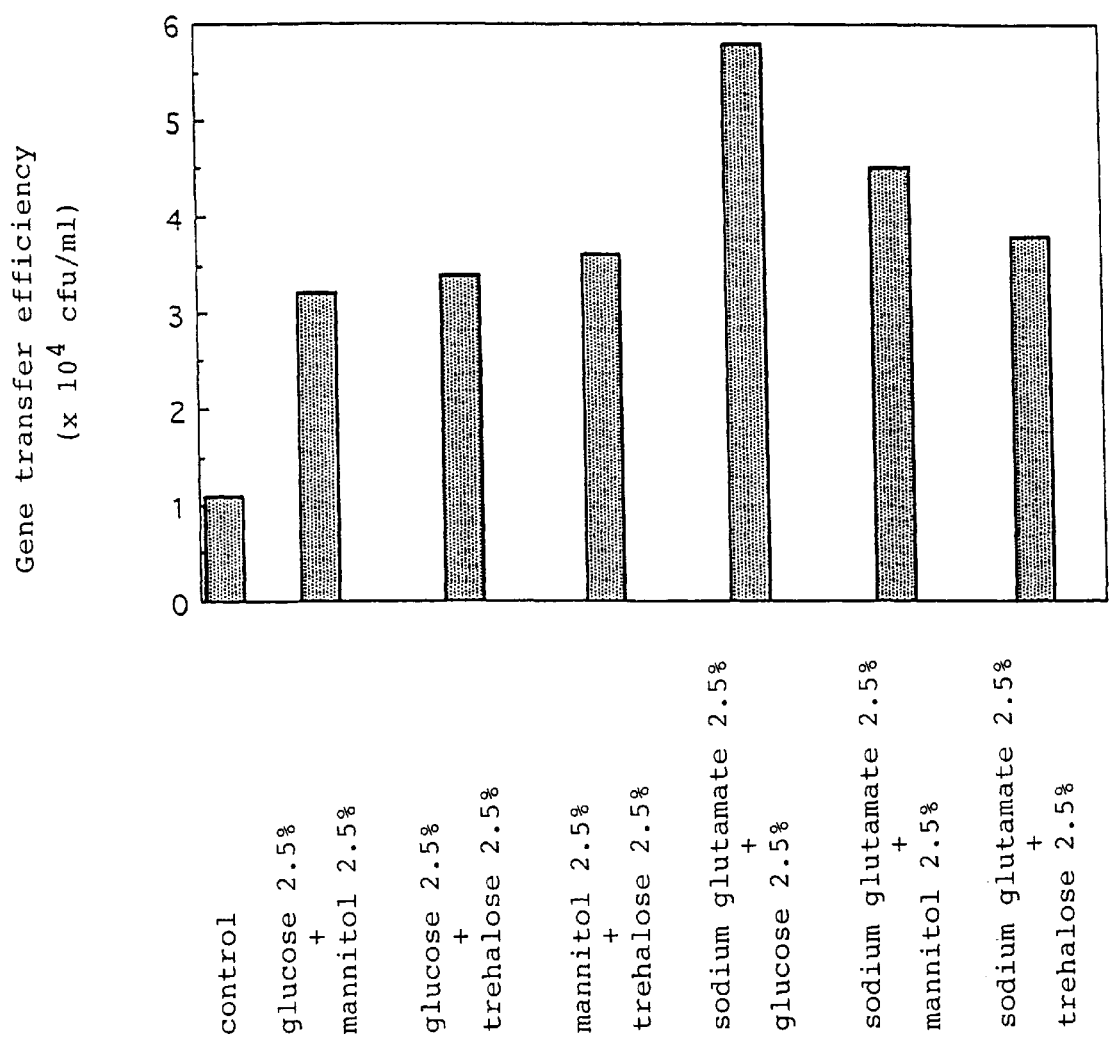
FIG. 3 is a graph which shows gene transfer efficiencies achieved by adding combinations of two additives each at a concentration of 2.5%.

To the virus vector stock solution obtained in Example 1 were added the amino acids, saccharides or combinations thereof as given in FIGS. 1 to 3 in such a manner as to give a final concentration of 5% or 2.5%. After freezing with liquid nitrogen, each sample was freeze-dried with a freeze-dryer (manufactured by Finaqua) over day and night. The freeze-dried product thus obtained was stored at −40° C. till using. As a control, an additive-free sample was also prepared. Each additive was a product manufactured by Wako Pure Chemical Industries, Ltd.

Example 3

Method for determining the titer (gene transfer efficiency) of recombinant MoMLV vector A cell culture dish (6 cm in diameter) was inoculated with 3T3 cells (manufactured by Dainippon Pharmaceutical Co., Ltd.). These cells were incubated in DMEM medium (manufactured by Gibco) containing 10% of fetal calf serum (manufactured by Gibco) under usual conditions (37° C., 5% $CO_2$) up to 80% confluence and then employed in the determination of the titer.

Distilled water for injection (manufactured by Otsuka Pharmaceutical Co., Ltd.) was added to each of the freeze-dried products obtained in Example 2 to thereby prepare a re-suspension of the vector having the same volume as the one before freeze-drying. 10 μl of this re-suspension of the vector was mixed with 990 μl of DMEM containing 10% of fetal calf serum to thereby give a vector solution for titer determination. From the 3T3 cells incubated up to 80% confluence, the medium was eliminated and 1,000 μl of the vector solution for titer determination was added thereto. After incubating the cells under the usual conditions for 4 hours, 3 ml of DMEM containing 10% of fetal calf serum was added thereto and the incubation was continued for additional 24 hours. Subsequently, the cells were incubated in DMEM containing 10% of fetal calf serum containing 800 μg/ml of G418 (manufactured by Gibco), i.e., an analog of neomycin. The number of the drug-resistant colonies thus formed was referred to as the titer (cfu/ml).

Example 4

Determination of the titer of recombinant MoMLV vector

FIG. 1 shows the results obtained by using various additives each at a concentration of 5%. Thus, it is revealed that glucose, sodium glutamate, mannitol and trehalose achieved high titers. FIGS. 2 and 3 show the results obtained by adding these additives each at a concentration of 2.5% and using combinations of two additives. These results indicate that a freeze-dried virus vector preparation with a high titer can be obtained by using sodium glutamate with glucose.

We claim:

1. A process for producing a gene transfer preparation which comprises adding an additive, which is a combination of glutamic acid or its sodium salt with glucose, to a recombinant virus vector followed by freeze-drying.

2. A process as claimed in claim 1, wherein each component of the additive is used at a weight ratio to the vector solution of from about 1% to about 10%.

3. A gene transfer preparation produced by a process as claimed in claim 1.

* * * * *